US010349934B2

(12) United States Patent
Pugh et al.

(10) Patent No.: US 10,349,934 B2
(45) Date of Patent: Jul. 16, 2019

(54) STITCHING DEVICE

(71) Applicant: Medtentia International Ltd Oy, Helsinki (FI)

(72) Inventors: Mark Pugh, Coolaney (IE); Ger O'Carroll, Co. Sligo (IE); Adrian Moran, Co. Sligo (IE)

(73) Assignee: Medtentia International Ltd. Oy, Helsinki (FI)

( * ) Notice: Subject to any disclaimer, the term of this patent is extended or adjusted under 35 U.S.C. 154(b) by 634 days.

(21) Appl. No.: 14/891,655

(22) PCT Filed: May 22, 2014

(86) PCT No.: PCT/EP2014/060547
§ 371 (c)(1),
(2) Date: Nov. 16, 2015

(87) PCT Pub. No.: WO2014/187901
PCT Pub. Date: Nov. 27, 2014

(65) Prior Publication Data
US 2016/0151063 A1    Jun. 2, 2016

(30) Foreign Application Priority Data

May 22, 2013  (EP) .................................. 13168785

(51) Int. Cl.
*A61F 2/24*    (2006.01)
*A61B 17/04*   (2006.01)
(Continued)

(52) U.S. Cl.
CPC ........ *A61B 17/0469* (2013.01); *A61F 2/2445* (2013.01); *A61F 2/2466* (2013.01);
(Continued)

(58) Field of Classification Search
CPC ............ A61B 17/0469; A61B 17/0482; A61B 2017/0472; A61B 2017/047
See application file for complete search history.

(56) References Cited

U.S. PATENT DOCUMENTS 7,879,049 B2* 2/2011 Dillon ................ A61B 17/0057
606/139
2006/0224169 A1* 10/2006 Weisenburgh, II ..........................
A61B 17/0401
606/153
2012/0215234 A1  8/2012 Chowaniec et al.

FOREIGN PATENT DOCUMENTS

EP       2263558 A2    12/2010

OTHER PUBLICATIONS

WIPO, International Preliminary Examining Authority (European Patent Office), International Preliminary Report on Patentability dated Oct. 5, 2015 in International Patent Application No. PCT/EP2014/060547, 15 pages.
(Continued)

*Primary Examiner* — Sarah A Simpson
(74) *Attorney, Agent, or Firm* — Inskeep IP Group, Inc.

(57) ABSTRACT

An annuloplasty stitching device (1) is disclosed for stitching at a stitch site in a patient. The stitching device comprises a support structure (2) comprising, an elongate center support (21) extending along an axial direction (27) between a proximal end and a distal end, a stitching arrangement (3) comprising, at least one elongate linkage section (31) being movably attached at a support end (25) of the linkage section to the center support, and at least one stitching member (32) arranged at a stitch end (26) of the linkage section and being movable along said axial direction by a pivoting action of the linkage section.

13 Claims, 13 Drawing Sheets

(51) Int. Cl.
*A61B 17/00* (2006.01)
*A61B 90/50* (2016.01)
(52) U.S. Cl.
CPC .............. *A61B 2017/00243* (2013.01); *A61B 2017/00783* (2013.01); *A61B 2017/047* (2013.01); *A61B 2017/0472* (2013.01); *A61B 2017/0498* (2013.01); *A61B 2090/506* (2016.02)

(56) References Cited

OTHER PUBLICATIONS

WIPO, European International Search Authority, International Search Report dated Nov. 27, 2014 in International Patent Application No. PCT/EP2014/060547, 6 pages.

* cited by examiner

STITCHING DEVICE

RELATED APPLICATIONS

This application is the U.S. National Phase of and claims priority to International Patent Application No. PCT/EP2014/060547, International Filing Date May 22, 2014, entitled Stitching Device, which claims benefit of European Application No. EP13168785.7, filed May 22, 2013 entitled Stitching Device, both of which are incorporated herein by reference in their entireties.

FIELD OF THE INVENTION

This invention pertains in general to the field of stitching devices for medical implants. More particularly the invention relates a single action stitching device and system for annuloplasty.

BACKGROUND OF THE INVENTION

It is known that todays stitching devices used for securing implants or the like in a body has a sewing-machine like arrangement. In such an arrangement a needle is projected from a container of some kind and the needle penetrates tissue before being retracted towards the container. This is repeated at least once more but with a displacement of the needle in a direction away from the first puncture site so as to create a loop with a thread attached to the needle wherein the implant can be arranged and secured. This means that the device needs to puncture the tissue at least two times to secure the implant which leads to unnecessary damaging of the tissue.

Other known stitching devices of today uses a bent needle which has a thread attached to it and where the bent needle is used to puncture the tissue with the thread. The bent needle is then angled to puncture the tissue once more returning the thread to the first side of the tissue allowing for an implant to be secured to the tissue. Such a solution requires that the spacing at the stitch site is large due to the need of the maneuvering of the needle.

US 2006/224169 disclose an instrument, assembly, and method for use in a procedure to effect anastomosis of a patient's bladder and urethra following a prostatectomy. The instrument comprises an instrument 3000, a tube assembly 3200, a driver opening rod 3260, an anchor driver assembly 3460, driver arms 3461 and anchors 700. The instrument is designed for small diameters in the urethra wherein the instrument needs to operate and the extension of the instrument radially from the center of the instrument is limited to tissue just outside the diameter of the urethra.

A problem with prior art devices is thus substantial tissue damage, difficulties in suturing sites with limited space, time consuming suturing due to the normal sequential approach and the large amount of individual punctures required for securing an implant.

The above problems may have dire consequences for the patient and the health care. Patient risk is increased.

Hence, an improved device for stitching would be advantageous, and in particular allowing for quicker stitching procedure, easier procedure in tight spaces, and less tissue damage, leading to reducing the time of lengthy surgery procedures, cost-effectiveness, and increased patient safety.

SUMMARY OF THE INVENTION

Accordingly, disclosures of the present invention preferably seek to mitigate, alleviate or eliminate one or more deficiencies, disadvantages or issues in the art, such as the above-identified, singly or in any combination by providing a device and a method that stitches at a stitch site, according to the appended patent claims.

According to aspects of the invention, a method, a system and a device for stitching are disclosed, whereby a single action stitch is achieved for stitching at a stitch site in a patient.

According to one aspect of the invention, a device is provided, a single action annuloplasty stitching device for stitching at a stitch site in a patient, comprising, a support structure comprising, an elongate center support extending along an axial direction between a proximal end and a distal end, a stitching arrangement comprising, at least one elongate linkage section being movably attached at a support end of the linkage section to the center support, and at least one stitching member arranged at a stitch end of the linkage section and being movable along said axial direction by a pivoting action of the linkage section.

According to another aspect of the invention, a system is provided comprising a stitching device of the first aspect of the invention and an implant. The stitching device having a thread guide being movably connected to a needle for being movable to an open state having an opening between the needle and the thread guide for forming a thread loop path around the implant.

According to another aspect of the invention, a method is provided, of using a stitching device comprising; arranging a stitching device at a stitch site in a patient wherein the stitching device is in a collapsed mode, expanding the stitching device comprising a support structure and a stitching arrangement comprising at least one stitching member comprising a thread to a deployed mode wherein the support structure is rotationally connected to the stitching arrangement and at least one stitching member are arranged parallel to the support structure, penetrating tissue at the stitch site by the at least one stitching member by moving the stitching device in a direction towards the tissue, and retracting the at least one stitching member from the tissue by moving the stitching device in an opposite direction from the direction towards the tissue securing the thread at the stitch site.

According to yet another aspect of the invention, a system for securing an implant is provided, comprising an implant and a stitching device comprising, a support structure comprising, an elongate center support extending along an axial direction between a proximal end and a distal end, a stitching arrangement comprising, at least one elongate linkage section being movably attached at a support end of the linkage section to the center support, and at least one stitching member arranged at a stitch end of the linkage section and being movable along said axial direction by a pivoting action of the linkage section.

Further disclosures of the invention are defined in the dependent claims, wherein features for the second and subsequent aspects of the invention are as for the first aspect mutatis mutandis.

Some disclosures of the invention provide for a stitching device having a small circumference.

Some disclosures of the invention also provide a stitching device tailored according to e.g. a stitching site and its physical characteristics, such as radius, shape, depth of penetration of at least one stitching member in the tissue at a tissue site.

Some disclosures of the invention provide for a stitching device tailored according to a path of arranging the stitching device at a stitching site.

Some disclosures of the invention also provide for a stitching device comprising a plurality of stitching arrangements allowing for a one-action stitching at multiple sites at once.

Some disclosures of the invention provide for a stitching device which is easily arranged at a stitching site and used for stitching.

Some disclosures of the invention also provide for a stitching member which is tightly arranged adjacent and parallel to a center support giving the stitching device a small circumference.

Some disclosures of the invention provide for a stitching device being easily guided to a stitching site through e.g. vessels, organs or similar.

Some disclosures of the invention provide for an elongate linkage section being arranged in a non-substantially perpendicular direction to a center support.

Some disclosures of the invention also provide for a stitching member being arranged in a non-parallel arrangement to a center support.

Some disclosures of the invention also provide for a stitching device having a simple and a less space obtaining expansion mechanism of the stitching device.

Some disclosures of the invention also provide for a stitching device expanded by moving an upper connection member relative to a lower connection member resulting in a movement of an elongate linkage section outwards from a center support.

Some disclosures of the invention provide for a stitching device which is made very slim for navigating the stitching device to a stitch site.

Some disclosures of the invention also provide for a stitching member having an increased stability in a direction parallel to a support member.

Some disclosures of the invention provide for a stitching device having a cross-sectional radius in a proximal-distal direction of the stitching device being reduced further.

Some disclosures of the invention also provide for a stitching member pivotally arranged at a stitch end of an elongate linkage section resulting in a stitching device having a small circumference in a collapsed mode.

Some disclosures of the invention also provide for a lower bar being slidably connected to a needle making it possible to control the needles rotation around an upper bar.

Some disclosures of the invention also provide for a control of an exposure of a thread by a position of a thread guide from a protective mode to a release mode.

Some disclosures of the invention also provide for a size of loops being based on a length of levers and their separation from a needle.

Some disclosures of the invention also provide for guiding a thread around an implant.

Some disclosures of the invention also provide for guiding an implant at the target site.

Some disclosures of the invention also provide for a method of using a stitch device to stitch at a stitch site having little room for stitching and/or where the path to the stitch site is narrow.

Some disclosures of the invention also provide for a method of a more stable and accurate penetration of a tissue.

Some disclosures of the invention also provide for a stitching device being arranged at a stitch site by e.g. twisting the implant into place, inserting, pushing, pulling or similar known methods.

Some disclosures of the invention also provide for an implant being arranged at at least one stitching member by e.g. twisting the implant into place, inserting, pushing, pulling or similar known methods.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which disclosures of the invention are capable of will be apparent and elucidated from the following description of disclosures of the present invention, reference being made to the accompanying drawings, in which.

DESCRIPTION OF THE PREFERRED DISCLOSURES

Figure 1:
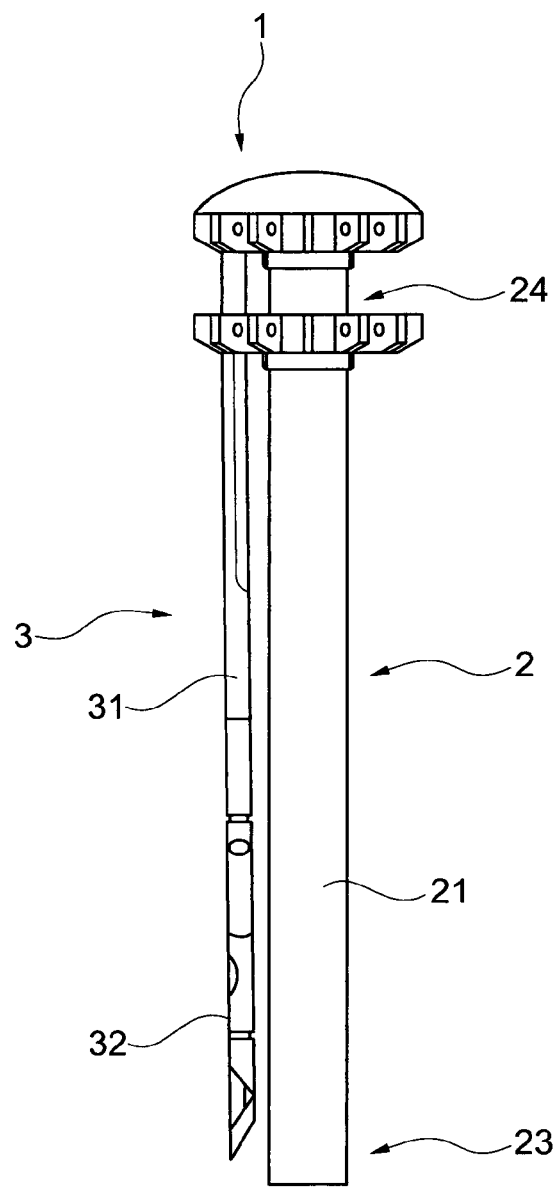
FIG. 1 is a side view of a stitching device in a collapsed mode.

Specific disclosures of the invention now will be described with reference to the accompanying drawings. This invention may, however, be embodied in many different forms and should not be construed as limited to the disclosures set forth herein; rather, these disclosures are provided so that this disclosure will be thorough and complete, and will fully convey the scope of the invention to those skilled in the art. The terminology used in the detailed description of the disclosures illustrated in the accompanying drawings is not intended to be limiting of the invention. In the drawings, like numbers refer to like elements.

The following description focuses on a disclosure of the present invention applicable to a stitching device and in particular to a stitching device for stitching at a stitch site in a patient. However, it will be appreciated that the invention is not limited to this application but may be applied to many other stitch sites including for example in an artery, vein and/or other organ than the heart.

In an example of the disclosure according to FIG. 1 is a single action stitching device 1 shown for stitching at a stitch site in a patient. The stitching device 1 comprises a support structure 2. The support structure 2 comprises an elongate center support 21 extending along an axial direction 27 between a proximal end 23 and a distal end 24. The stitching device 1 further comprises a stitching arrangement 3 comprising, at least one elongate linkage section 31 being movably attached at a support end of the elongate linkage section 31 to the center support 21 and at least one stitching member 32 arranged at a stitch end of the elongate linkage section 31 and being movable along said axial direction by a pivoting action of the elongate linkage section 31. By using the stitching device 1 according to the disclosure above, the stitching device 1 has a small circumference and can be tailored e.g. according to a stitching site and its physical characteristics, such as radius, shape, depth of penetration of the at least one stitching member 32 in the tissue at the tissue site and so on. More particularly, the pivoting action of the linkage section allows for a compact device that can be easily navigated to the target site while at the same time having sufficient radial reach to suture for example an annuloplasty device, such as an annuloplasty ring. The length of the linkage section 31 may thus substantially correspond to at least the radius of an annuloplasty implant such as an annuloplasty ring 50 illustrated in FIGS. 9-12. This solves an important problem with prior art devices that on the contrary are focused on reconnection of tissue in anastomosis procedures where the device is accordingly adapted to have as small foot-print as possible, i.e. by suturing as closely to the insertion opening as possible in order to be able to rejoin the tissue.

Figure 12:
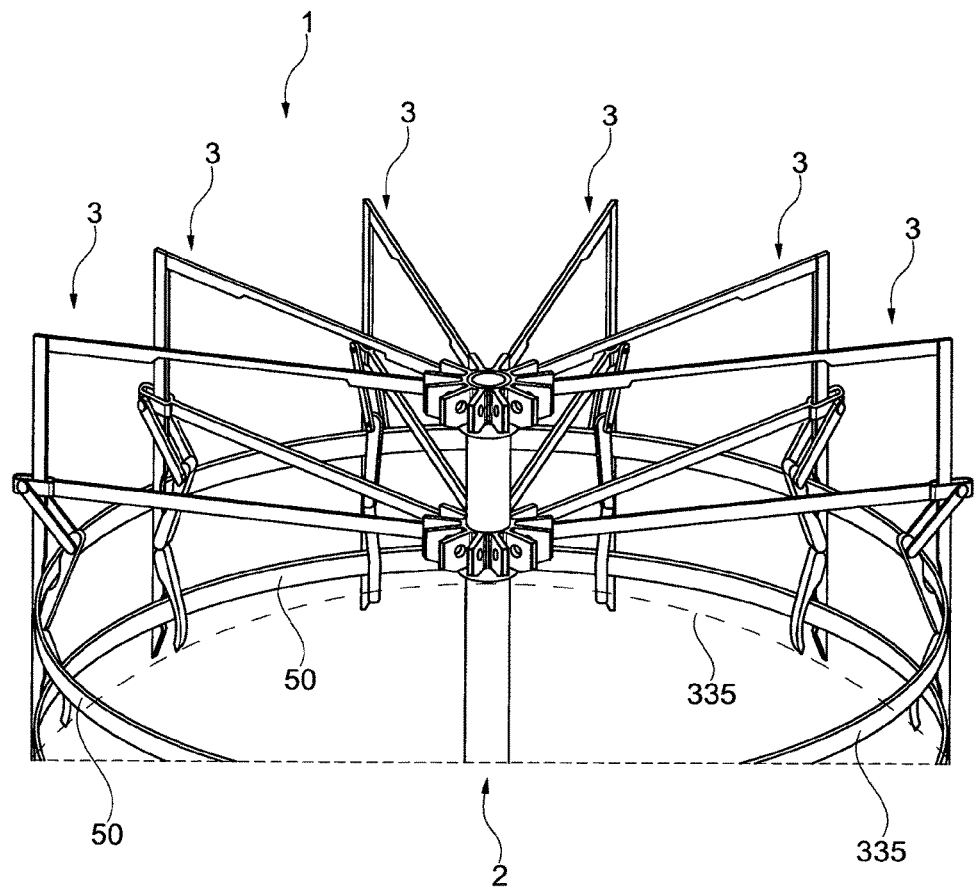
FIG. 12 is a side view of a stitching device comprising plurality of stitching members having an implant inserted through the stitching members.

Further, as the length of the linkage section 31 may substantially correspond to at least the radius of an annuloplasty implant it allows for simultaneous stitching at several locations around the circumference of the ring 50 when the stitching device 1 is positioned in the center of the ring 50 as illustrated in FIG. 12. The reach of the elongate linkage section 31 may also be varied by adjusting the angle of the same relative the support 2, in order to adapt to annuloplasty rings of varying diameters. Further, the stitching device 1 may be tailored according to a path of arranging the stitching device 1 at the stitching site. The path may have varying diameters, obstacles along the path which need to be circumvented in a special way which may be used to tailor the stitching device 1. In one example illustrated in FIG. 12, the stitching device 1 comprises a plurality of stitching arrangements 3. By having the stitching device 1 comprising the plurality of stitching arrangements 3, an operator can in one-action, i.e. in one movement of the stitching device 1, make a plurality of stitches. This reduces time for the operator which gives the operator time to proceed with other activities related to the stitching and/or life saving operations. In one example the tailoring is achieved by a specific arrangement of the plurality of stitching arrangements 3 on the center support 21 e.g. so that obstacles along the path to the stitch site are avoided and/or to be customized for a specific shape of the tissue site.

Figure 2:
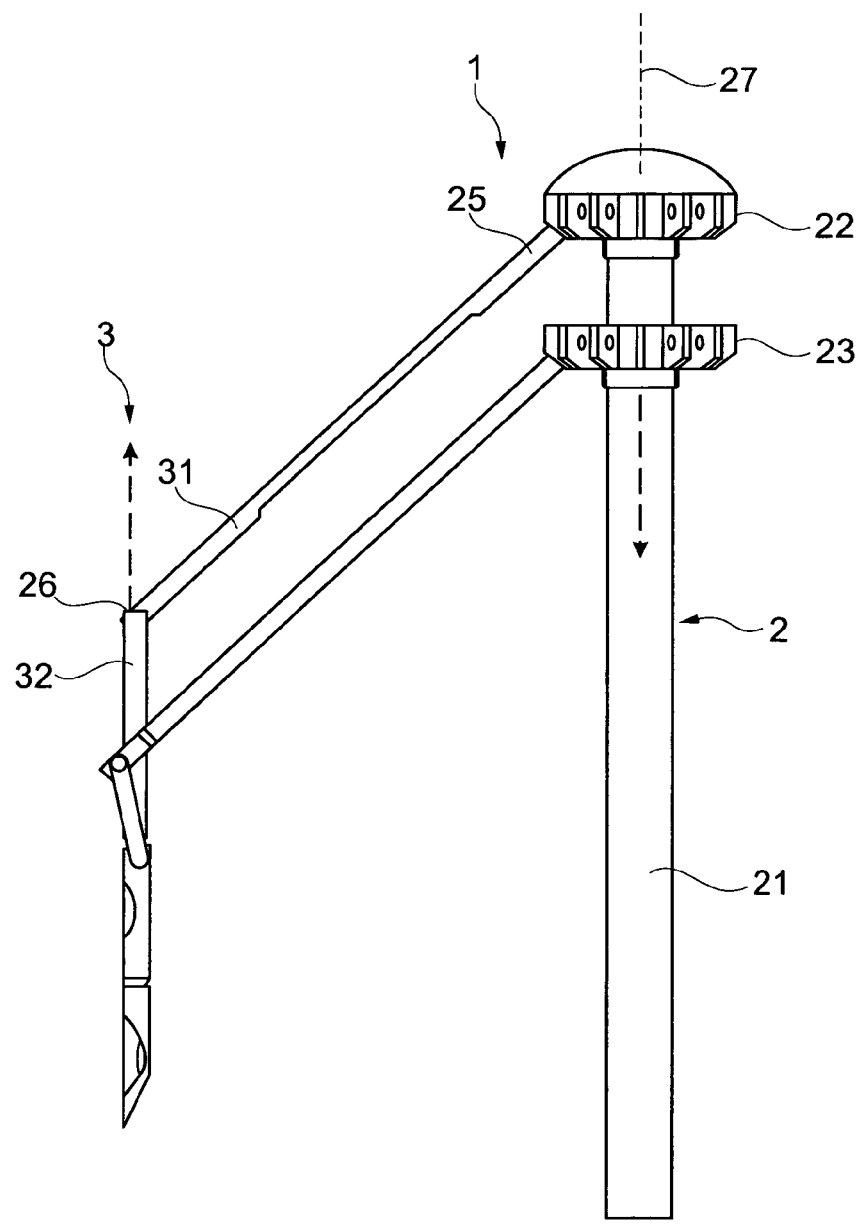
FIG. 2 is a side view of a stitching device in a semi-expanded mode.
Figure 3:
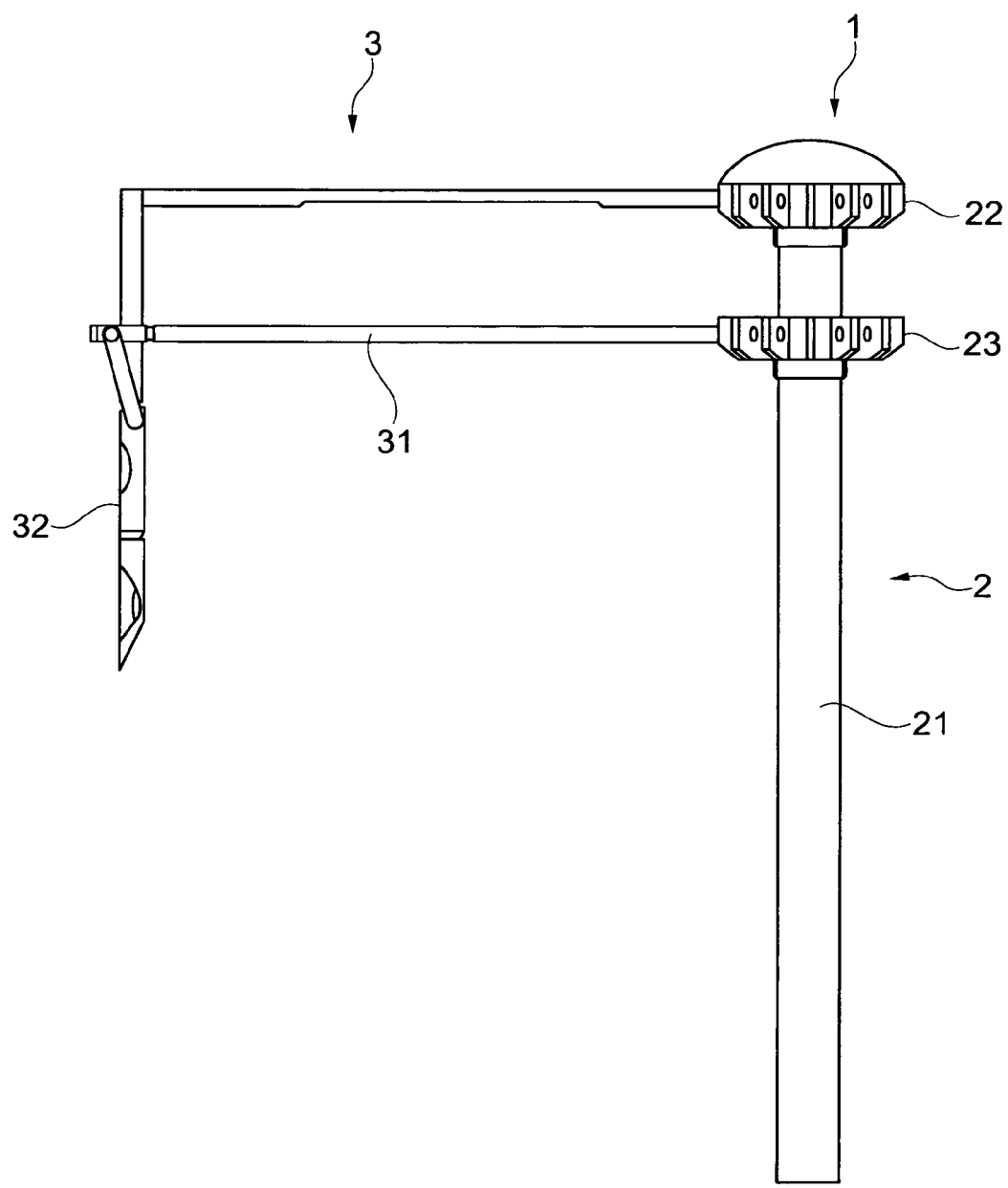
FIG. 3 is a side view of a stitching device in a semi-expanded mode.

In another example illustrated in e.g. FIGS. 1-3 the stitching arrangement 3 is movably arranged from a collapsed mode, wherein the at least one elongate linkage section 31 is parallel arranged adjacent to the elongate center support 21 of the support structure 2, to a deployed mode, wherein the at least one elongate linkage section 31 is arranged substantially perpendicular to the center support 21 and the at least one stitch member 32 is arranged substantially parallel to the center support 21 of the support structure 2. By having the stitching arrangement 3 being movable from a collapsed mode wherein the stitching device 1 is capable of being navigated to a stitch site, to a deployed mode wherein the stitching device 1 is deployed for stitching, the stitching device 1 is easily arranged at a stitching site and used for stitching. In the collapsed mode the center section 21 and the stitching member 32 is tightly arranged adjacent and parallel to the center support 21 giving the stitching device 1 a small circumference, such as 0.5-5 cm, which allows the stitching device 1 to be easily guided to the stitching site through e.g. vessels, organs or similar. When positioned at the stitching site the stitching device 1 is arranged in the deployed mode by the elongate linkage section 31 is arranged substantially perpendicular to the center support 21 and the stitching member 32 is arranged parallel to the center support 21. In other examples the elongate linkage section 31 is arranged in a non-substantially perpendicular direction to the center support 21 and/or the stitching member 32 is arranged in a non-parallel arrangement to the center support 21 in the collapsed mode and/or expanded mode.

Figure 4:
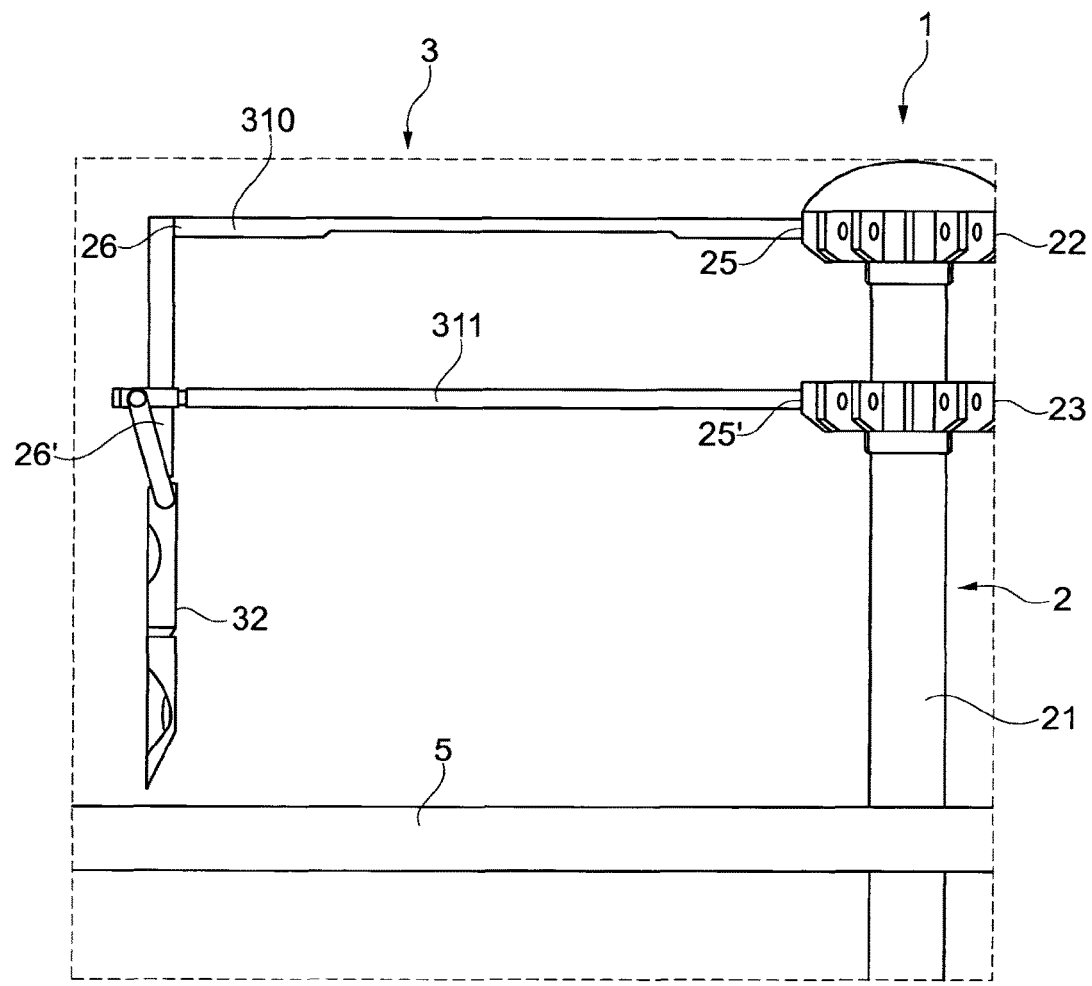
FIG. 4 is a side view of a stitching device in an expanded mode at a stitch site.

In an example illustrated in e.g. FIGS. 3 and 4 (3.) the support structure 2 further comprises an upper connection member 22 arranged at the center support 21 and closer to the distal end of the center support 21 than a lower connection member 23 arranged at the center support 21. The upper and/or lower connection members are connected to the at least one elongate linkage section, and the upper 22 and lower connection members 23 are movable relative to each other resulting in the pivoting action, as also seen in FIG. 2 (dashed arrows). By having the support structure 2 further comprising the upper 22 and lower connection member 23, the stitching device 1 is expanded by moving the upper connection member 22 relative to the lower connection member 23 resulting in a movement of the elongate linkage section 31 outwards from the center support 21, i.e. the pivoting action. This allows for a simple and a less space obtaining expansion mechanism of the stitching device 1. In an alternative example the upper 22 and lower connection member 23 is moved relative to each other by having the upper connection member 22 being fixed arranged at the distal end of the center support 21 wherein the center support 21 has a tubular shape such as a tube, guide wire or similar. The lower connection member 23 is arranged on a sleeve, slidable on the exterior of the tubular shaped object allowing for the upper 22 and lower connection member 23 to be moved relative to each other. In another example the lower connection member 23 is fixed arranged and the upper connection member 22 is movable relative to the lower connection member 23.

Figure 5:
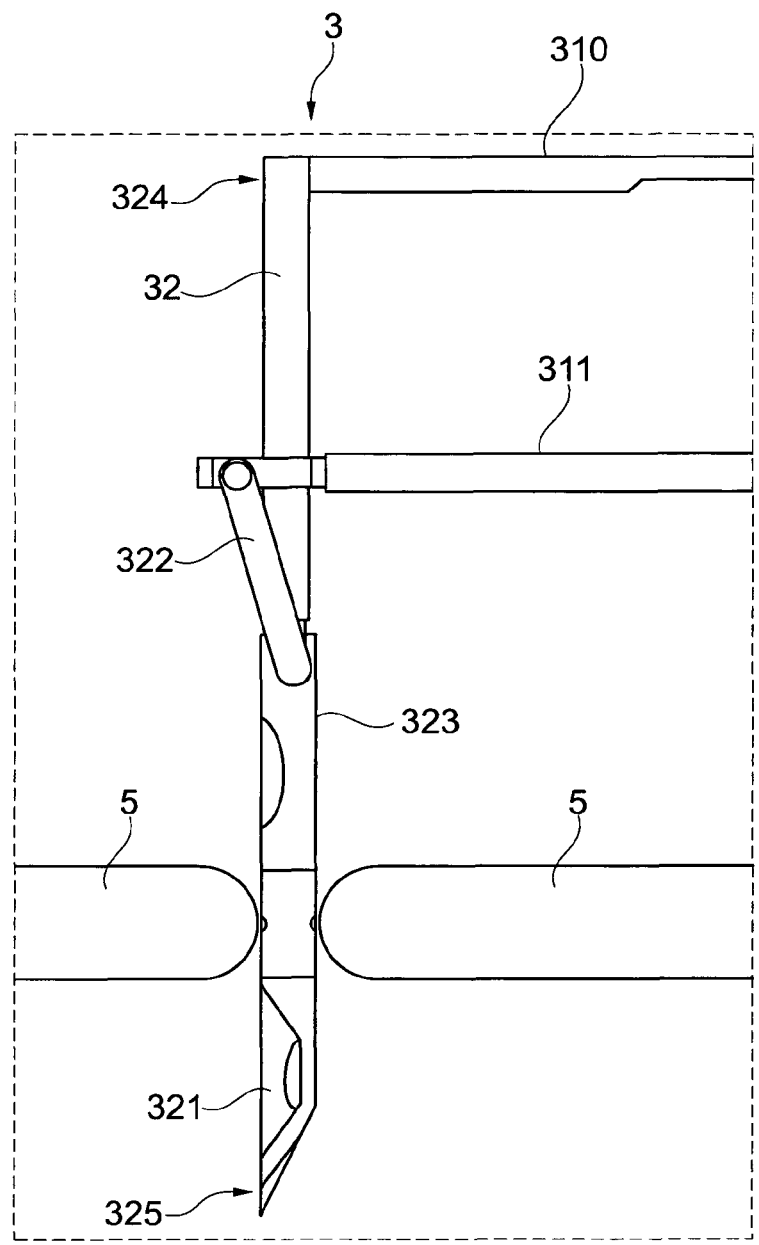
FIG. 5 is a side view of a stitching device in an expanded mode penetrating tissue at a stitch site.

In another example illustrated in e.g. FIGS. 4 and 5 each of the at least one elongate linkage sections 31 comprises, an upper bar 310, wherein the upper bar 310 is rotationally connected to the upper connection member 22 at a support end of the upper bar 310, a lower bar 311, wherein the lower bar 311 is rotationally connected to the lower connection member 23 at a support end of the lower bar 311, and wherein the two bars 310 and 311 are connected to the stitching member 32 at respective stitch ends allowing for the stitching member to be movable along said axial direction by moving said upper and lower connection members. This also allows for the stitching member 32 to be arranged parallel to the center support 21 of the support structure 2. By using the elongate linkage section 31 comprising the two bars 310 and 311 that are rotationally connected to the upper 22 and lower connection member 23 and connected to the stitching member 32, the stitching device 1 is made very slim for navigating the stitching device 1 to the stitch site. At the same time the stitching device 1 is extendable outwards for being deployed and stitching is to be performed. Additionally, the upper 310 and lower 311 bar construction gives the stitching member 32 an increased stability in a direction parallel to the support member 2, i.e. the stitching member 32 does not easily bend or flex in a direction other than the desired direction towards the tissue when being pressed against the tissue.

In yet another example as illustrated in FIG. 1 the upper bar 310 comprises a recess along at least a part of its length and wherein the recess is large enough to partly surround the lower bar 311 in the collapsed mode. By having the upper bar 310 comprising a recess that at least partly is capable of surrounding the lower bar 311 in the collapsed mode, the stitching device 1 has an even smaller circumference than without the recess. Hence, the cross-sectional radius in a proximal-distal direction of the stitching device 1 is reduced further. The recess is in an example formed by making the upper bar 310 having a cut out along its entire length and where the cut out has its opening towards the lower bar 311 so that the lower bar 311 is retracted into the upper bar 310 when collapsed. In another example the recess is only partially formed along the length of the upper bar 310.

In an example illustrated in FIGS. 1-3 the at least one stitching member 32 is pivotally arranged at the stitch end of the elongate linkage section 3. By having the stitching member 32 pivotally arranged at the stitch end of the elongate linkage section 3, the stitching device 1 is made with a smaller circumference in the collapsed mode than if the stitch member is fixed arranged at the stitch end of the linkage section 3. In another example the stitching member 32 is fixed arranged at the stitch end of the elongate linkage section 3.

Figure 6:
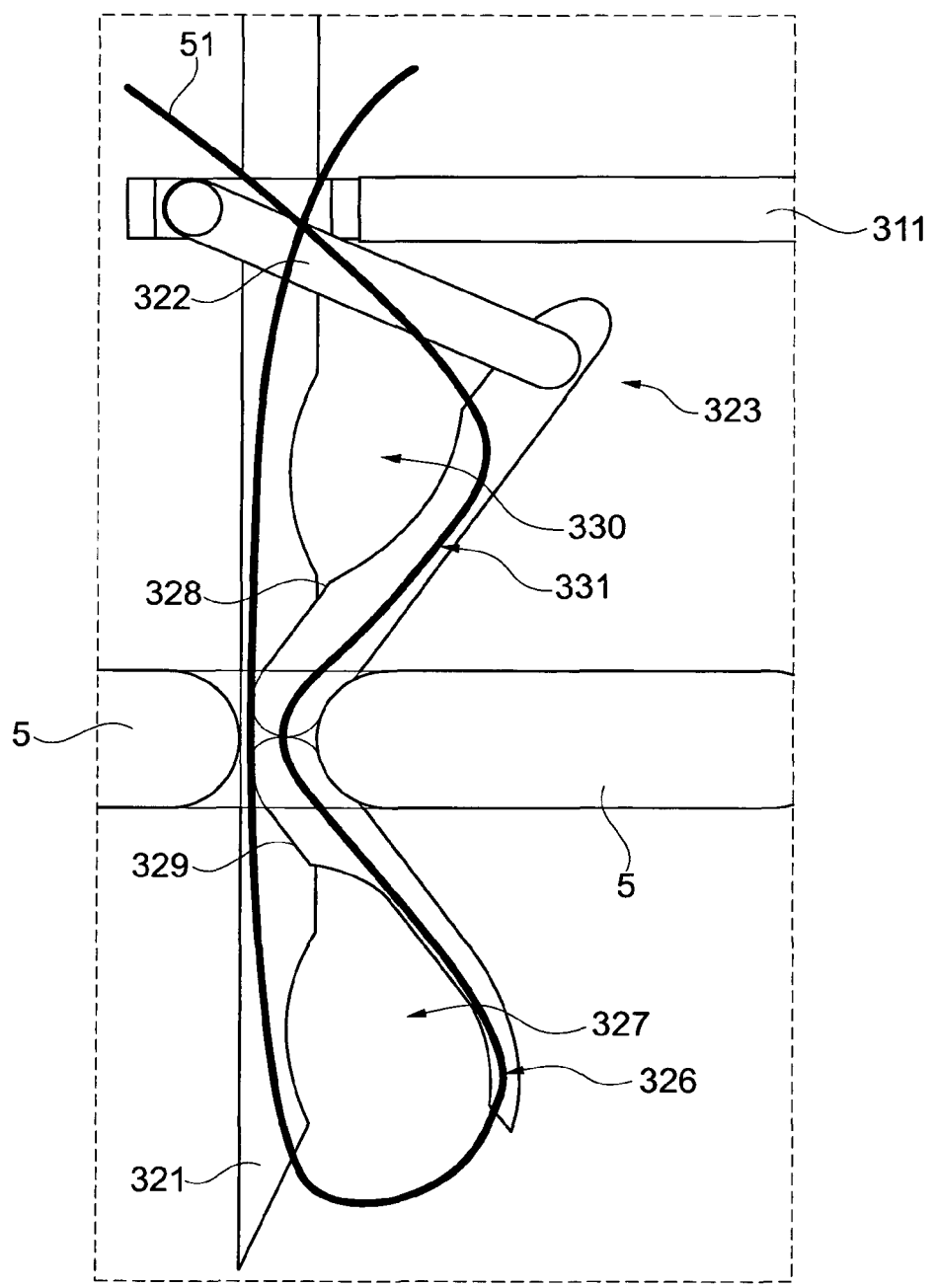
FIG. 6 is a side view of a stitching device comprising two loops.
Figure 7:
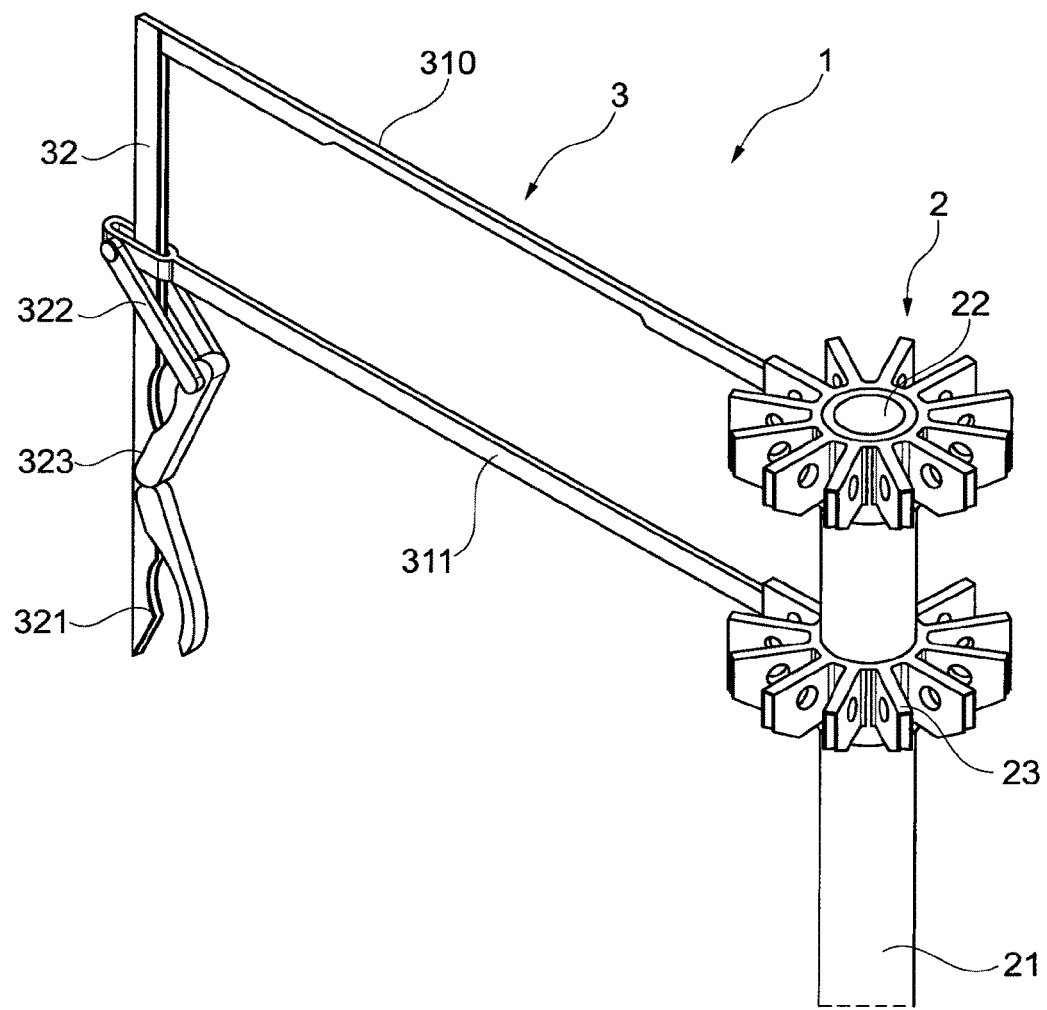
FIG. 7 is another side view of a stitching device in an expanded mode.
Figure 9:
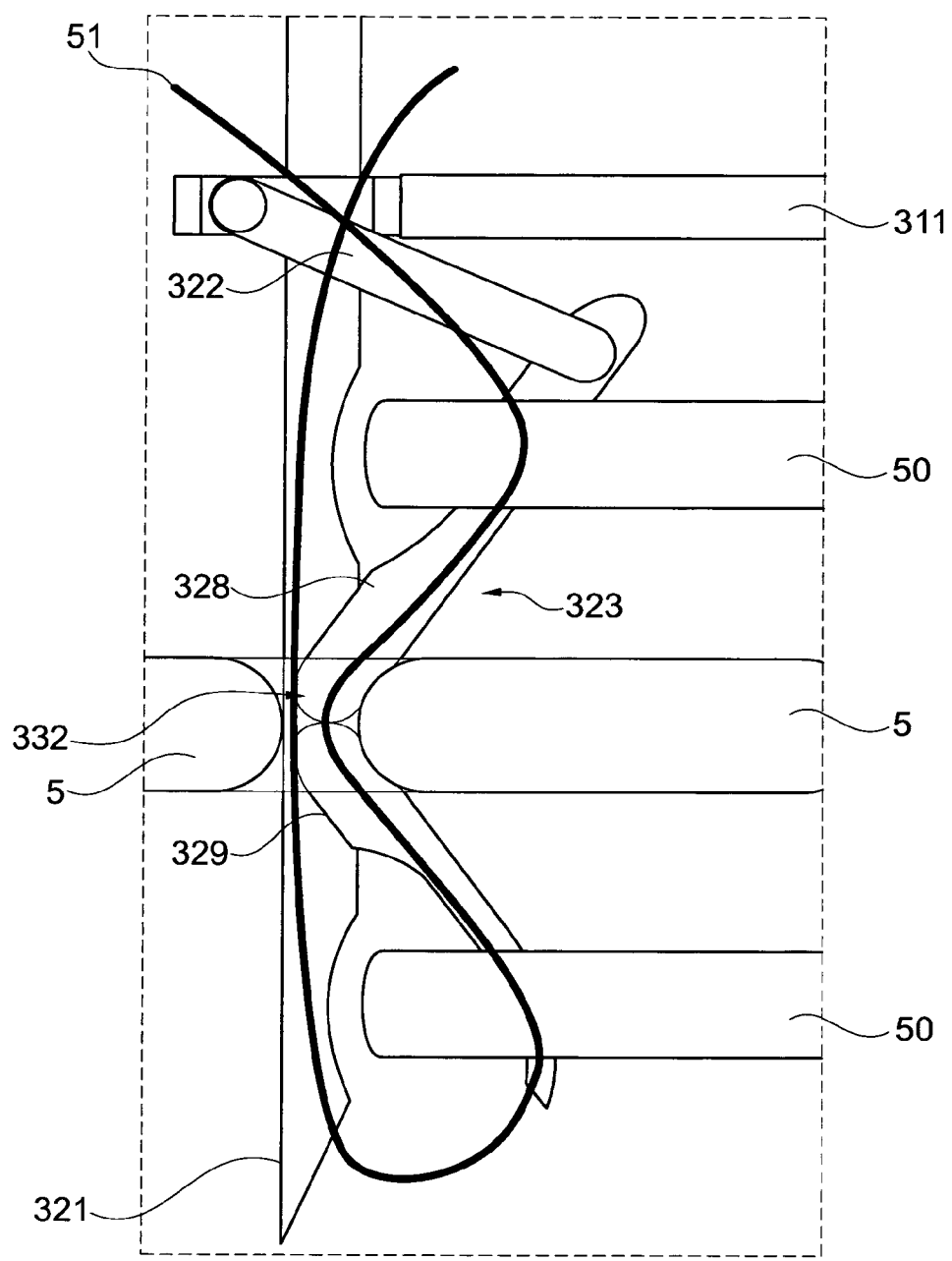
FIG. 9 is a side view of a stitching device comprising two loops having an implant inserted through the loops.
Figure 10:
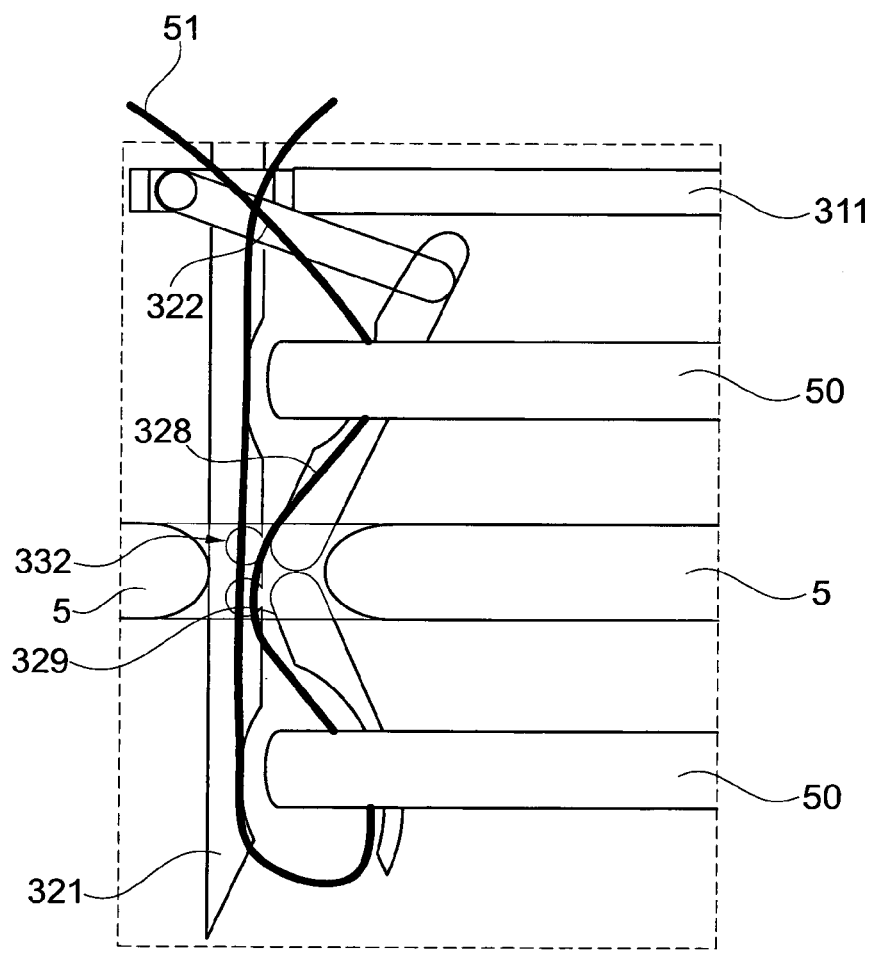
FIG. 10 is a side view of a stitching device comprising a thread guide released from a stitching member for securing an implant.

In an example illustrated in e.g. FIGS. 6, 9, 10, the stitching member comprises a needle 321 and a thread guide 323 for a thread 51. The thread guide may be movably connected to the needle or the linkage section for being movable to an open state having an opening 327 between the needle and the thread guide for forming a thread loop path 326 around the opening 327. The thread guide therefore allows for guiding the thread 51 around an implant 50 and simultaneous guide the implant itself by being inserted into the opening 327. The opening 327 may be adapted to receive and guide e.g. an annuloplasty implant. Hence, once the stitching member has punctured the tissue (FIG. 5), the thread guide 323 may be opened for exposing opening 327 (FIG. 6), and an implant 50 may be inserted, e.g. rotated, into the opening (FIG. 9), such that the thread loops the implant.

The thread guide may comprise at least two guide levers 328, 329, rotationally joined at a respective joining end, whereby the guide levers are movable to an open state having a first and a second opening 327, 330, for providing a first and a second thread loop path 326, 331, around said openings. Hence, the thread guide may provide several loops for e.g. for a helix-shaped annuloplasty implant with rings at each side of a heart valve, as illustrated in FIG. 9.

By having the thread guide 323 comprising the two guide levers 328 and 329 and having them rotationally joined, the thread guide 323 is collapsed adjacent to the needle 321 in the protective mode when penetrating the tissue and in the release mode, two loops are created by the two guide levers 328 and 329. One loop is created between the lever 322, the guide lever 328 and the needle 321. The other loop is created between an end which is opposite of the joining end of the guide lever 329 closest to the sharp end of the needle 321 which is expanded outwards from the sharp end of the needle 321 and the sharp end of the needle 321. This allows the operator to create loops of with the thread 51 wherein the implant 50 can be inserted through for securing of the same. In an example, one loop is created on one side of the tissue 5 and the other on the other side on the tissue 5. Alternatively, the two loops are created on the same side of the tissue 5. The size of the loops is preferably chosen to be of a size that allows the implant 50 to be inserted through the loops. The length of the levers 328 and 329 and their separation from the needle 321 decides the size of the loops.

Each of the respective joining ends may be pivotably connected to the needle at a pivoting joint (332), whereby the at least two guide levers may be movable to a closed state in which the at least two guide levers are parallel to the needle. The thread guide 323 may thereby be folded to a compact state by being aligned along the needle when not expanded. This allows for a single puncture in the tissue, producing less tissue damage.

In an alternative example illustrated in e.g. FIGS. 9 and 10 the at least two guide levers 328 and 329 are releasable connected to the needle 321 at the pivoting joint 332, at their joining ends. By having the two levers 328 and 329 releasable connected to the needle 321 at their joining ends, an easy release and tightening mechanism is achieved for the thread 51 to be tightened and released from the stitching device 1, as seen in FIG. 10, where the thread guide 323 is released from the needle 321, and in FIG. 11 where the thread has been tightened.

In one example illustrated in FIG. 10 the needle 321 comprises a cut-out at the pivoting joint 332 for releasable connecting the thread guide 323. Other commonly used and known arrangements for releasable connecting a linkage, such as the thread guide 323 to a tubular object, such as the needle 321 may also be used within the scope of this disclosure. The cut-out secures the thread guide 323 in the needle 321 during the stitching and when stitching has completed the thread guide is then released from the needle 321 to allow the thread 51 to be maintained at the stitch site while retracting the needle 321 from the tissue.

The thread guide 323 may be rotationally linked to the linkage section 31, whereby the thread guide is movable to the open state by moving the linkage section. This provides for operating the thread guide via the linkage section or the connection members 22, 23, that are joined to the linkage section 31.

In yet an example illustrated in FIG. 5 each of the at least one stitching members 32 comprises a needle 321 with a blunt end and a sharp end, and wherein the blunt end is rotationally connected to the upper bar 310 and wherein the lower bar 311 is slidable connected to the needle 321 closer to the sharp end than the upper bar 310, allowing for the needle 321 to be arranged parallel to the center support 21 of the support structure 2 in the collapsed mode and in the deployed mode. By having the needle 321 rotationally connected at the blunt to the upper bar 310, the needle 321 can be rotated around an axis of the upper bar 310. By having the lower bar 311 slidable connected to the needle 321 it is possible to control the needles 321 rotation around the upper bar 310 by moving the lower bar 311 up and/or down to angle the needle 321 into the desired position parallel to the center support 21. The needle 321 is alternatively angled to another position if desired by the operator. Such positions can be between 1-45 degrees, allowing the operator to make a stitch angled outward from the center support 21. Such angled stitching could be useful when securing an implant 50 such as an annuloplasty implant or similar, inside a vein, an artery, organ or similar where the needle 321 cannot be arranged above or below, with the parallel position, at the stitch site due to limited space around the stitching device 1. Then the angled needle position is useful for stitching in the tissue to secure the implant 50.

Figure 8:
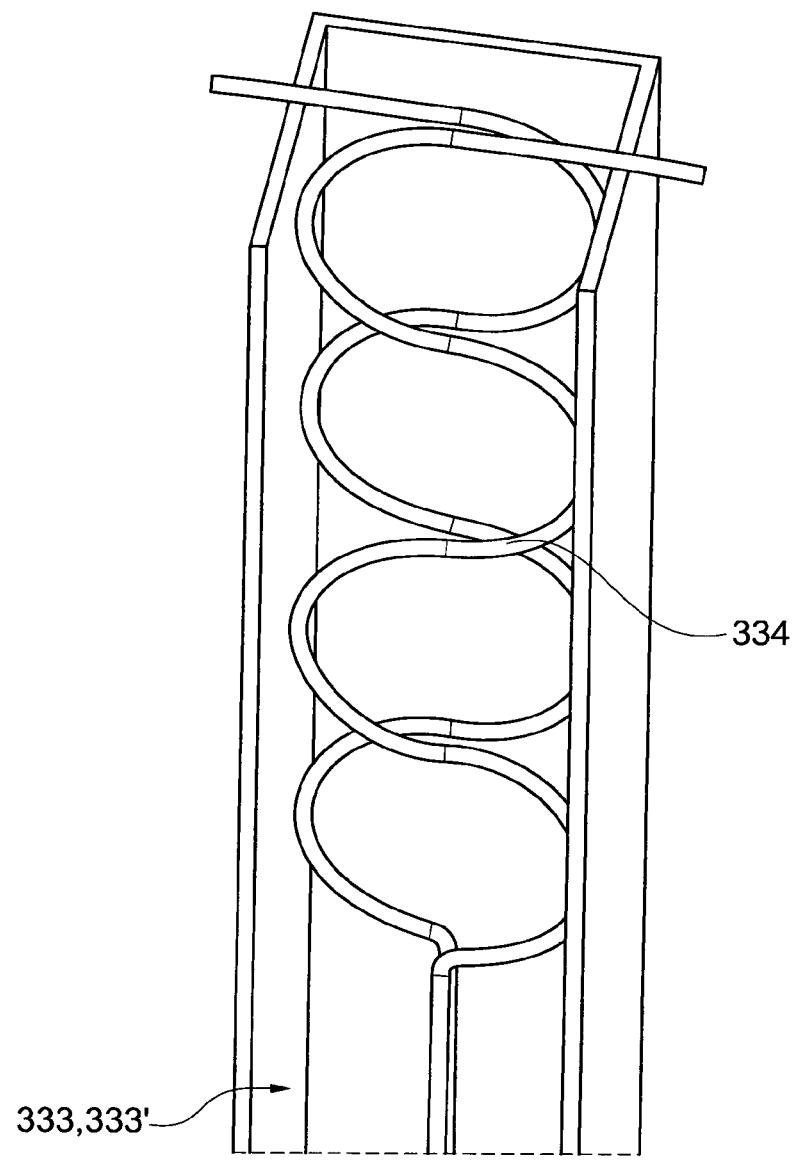
FIG. 8 is a side view of a member comprising a thread.
Figure 11:
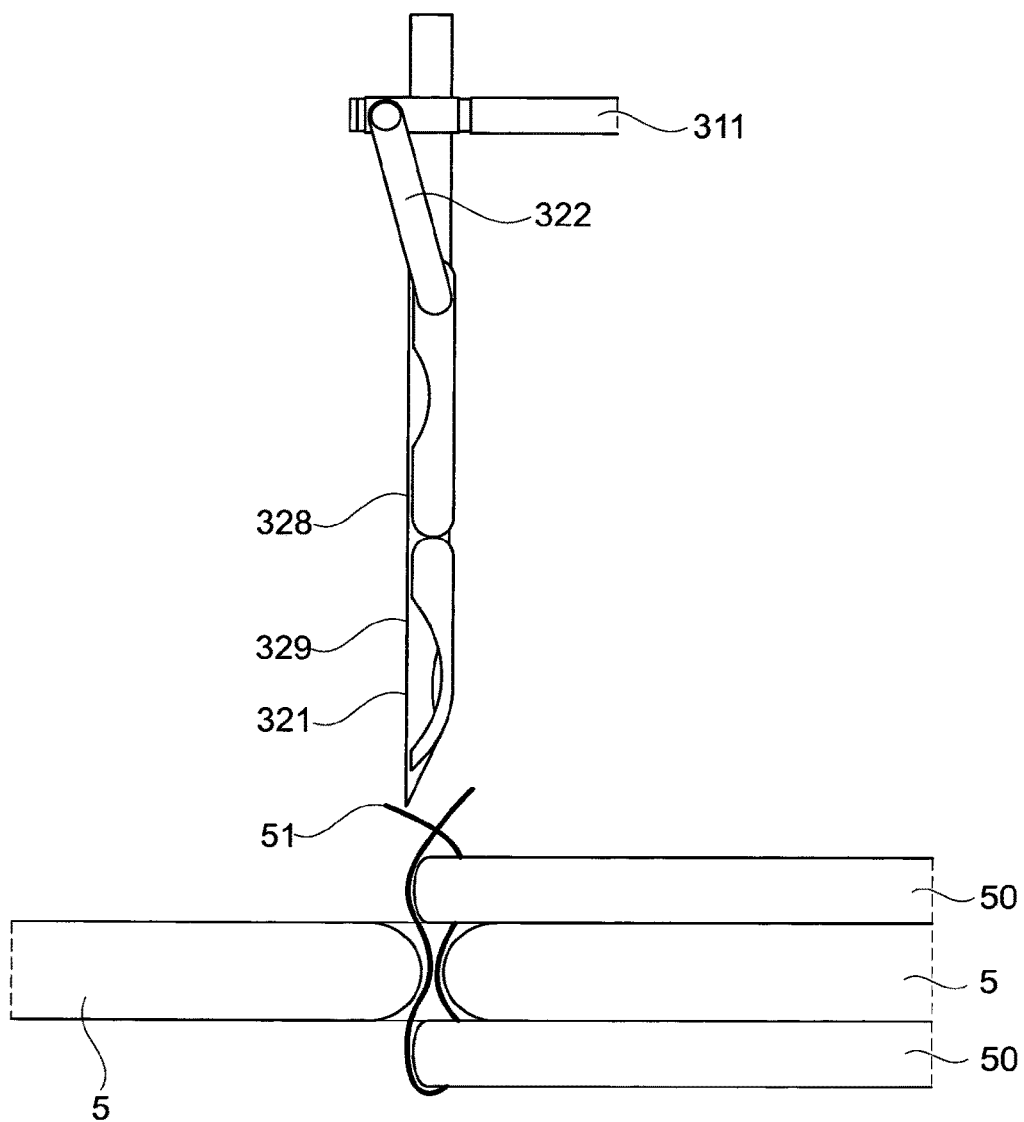
FIG. 11 is a side view of a stitching device having secured an implant at a stitch site.

The needle 321 and/or said thread guide 323 may comprise a cut-out 333, 333', as illustrated in FIG. 8 for receiving the thread inside. The cut-out may releasably securing the thread 51. The releasable securing of the thread may be provided by a clamping element 334 that applies a pressure on the thread. The thread can be pulled out of the clamping element 334 by applying a force. Hence, when the thread guide is released from the needle, as seen in FIG. 10, the thread 51 can also be released from the thread guide, and from the needle, so that the thread guide and from the needle can be retracted and leaving the thread in place around the implant 50 (FIG. 11). By having the stitching linkage comprising the thread 51 in the cut-out, the thread 51 is protected from getting stuck or otherwise be affected in an undesired way.

The stitching device (1) may comprise a plurality of stitching arrangements 3 connected to the support structure such that said stitching members are arranged along a three-dimensional path 335 along which an implant partially extends. Various implants can thus be stitched in place by having multiple stitching members 32 stitching simultaneously along the extent of the implant 50.

In an example illustrated in e.g. FIGS. 5 and 6 the stitching member 32 further comprises a lever 322 with a bar end and a thread guide end, a thread guide 323 with a lever end and a thread end for controlled deployment of a thread 51, wherein the bar end of the lever 322 is rotationally connected to the stitch end of the lower bar 311 and wherein the thread guide end of the lever 322 is rotationally connected to the lever end of the thread guide 323 and wherein the thread guide 323 is releasable connected to the needle 321. By having the lever 322 and the thread guide 323 rotationally connected to each other and where the thread guide 323 is releasable connected to the needle 321, the thread guide 323 is controlled by further movement of the lower bar 311 and allows for the thread guide 323 to separate from the needle 321. Hence, the operator can control the exposure of the thread 51 by the position of the thread guide 323 from a protective mode to a release mode. In the protective mode the needle 321 and the thread guide 323 protects the thread 51 from the surroundings and are arranged adjacent to each other and/or overlapping each other. In the release mode the thread 51 is exposed to the surroundings when the thread guide 323 is separated with a distance from the sharp end of the needle 321 and/or the needle 321. This is accomplished by moving the lower bar 311, which is rotationally connected to the bar end of the lever 322 which in turn is rotationally connected to the thread guide 323, in a direction towards the sharp end of the needle 321 which separates the thread guide 323 and the needle 321 from each other. Further movement towards the sharp end releases the thread guide 323 from the needle 321.

In an example the stitching device 1 as described above is a part of a system comprising the implant 50. The system thus comprises an implant and a stitching device having a thread guide 323 being movably connected to a needle 321 for being movable to an open state having an opening 327 between the needle and the thread guide for forming a thread loop path around the implant.

In an example the stitching device 1 is a part of a system comprising the implant 50 and a guiding device for the implant 50. Such implants and guiding systems could be annuloplasty implants and their accompanying guiding device.

Figure 13:
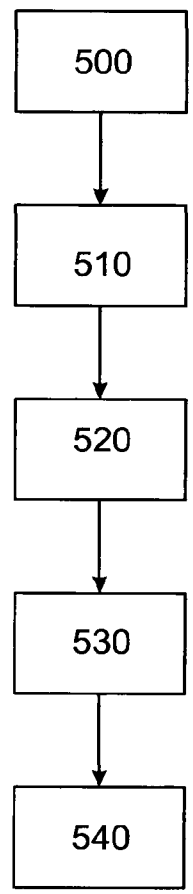
FIG. 13 is a flow chart of a method of using a stitch device.

In an example of a method of illustrated in FIG. 13 using a stitching device 1 comprises arranging 500 the stitching device 1 at a stitch site when the stitching device 1 is in a collapsed mode, as illustrated in FIG. 1. Following, expanding 510 the stitching device 1 comprising a support structure 2 and a stitching arrangement 3 comprising at least one stitching member 32 comprising a thread 51 to a deployed mode wherein the support structure 2 is rotationally connected to the stitching arrangement 3 and the at least one stitching member 32 is arranged parallel to the support structure 2, as illustrated in FIG. 3. Penetrating the tissue 520 at the stitch site with the at least one stitching member 32 by moving the stitching device 1 in a direction towards the tissue 5, as illustrated in FIG. 5. Retracting 530 the at least one stitching member 32 from the tissue 5 by moving the stitching device 1 in an opposite direction from the direction towards the tissue 5 securing the thread 51 at the stitch site. By using the above method it is possible to stitch at a stitch site having little room for stitching and/or where the path to the stitch site is narrow. The arrangement of the stitching device 1 at the stitch site is performed by an operator such as a surgeon or the like capable of navigating the stitching device 1. The navigation by the operator may comprise pushing, pulling, twisting, bending or similar operations commonly used to navigate a medical device in a body of a patient.

When the stitching device 1 is at the stitching site the operator expands the stitching device 1 to the deployed mode wherein the at least one stitching member 32 is arranged to be penetrated through the tissue 5 at the stitch site. The expansion of the stitching device to the deployed mode is in an example performed by moving the lower connection member 23 towards the upper connection member 22. This is achieved by e.g. pushing on the lower connection member in a proximal to distal direction of the center support 21 such as, by having a sheet arranged on the center support 21. In another example the movement of the lower connection member 23 is performed by pulling the lower connection member 23 towards the upper connection member 22 such as, by pulling in a wire arranged inside the center support 21. In other examples the same mechanisms are used for moving the upper connection member 22 towards the lower connection member 23. This relative movement between the upper 22 and lower 23 connection members results in the pivoting action of the stitching arrangement 3 so that it expands outwards form the center support 21.

In one example the penetration of the tissue 5 at the stitch site is achieved by pushing the stitching device 1 towards the tissue. In another example the penetration of the tissue 5 at the stitch site is achieved by pulling the stitching device 1 towards the tissue. In yet other examples the upper 22 and lower 23 connection members are pushed or pulled jointly while maintaining the center support 21 in a fixed position such as pressed against the tissue, in order to penetrate the tissue with the at least one stitching members 32. By having the center support 21 fixed arranged against the tissue a more stable and accurate penetration of the tissue is achieved since the stitching device 1 is secured from movement. Additionally, the operator is given the possibility to re-secure the stitching device 1 if unsatisfied of its location before penetrating the tissue with the at least one stitching member 32 and thus the damage to the tissue can be kept to a minimum compared to when the operator moves the stitching device 1 and partly penetrates the tissue before re-securing it to a desired location.

The retraction of the at least one stitching member 32 from the tissue 5 to secure the thread at the stitch site is performed in one example by moving the stitching device 1 in an opposite direction from the penetrating direction, as discussed above. In another example the at least one stitching member 32 is retracted by movement of the at least one stitching member 32.

In another example the retracting 530 of the at least one stitching member 32 further comprises releasing at least one thread guide being rotationally connected to said stitching member from a needle, whereby the thread guide guides the thread. By releasing the thread guide 323 from the needle 321, wherein both the needle 321 and the thread guide 323 comprises the thread 51, the thread 51 is released from the stitching device 1 at the stitch site by the operator in a controlled way.

In an example the method further comprises arranging an implant (50) at the thread guide, and guiding 540 the thread around the implant. By arranging the implant 50 at the thread 51 and the at least one stitching member, the implant is also secured when the thread is secured by retraction of the at least one stitching member 32. After penetrating the tissue 5 the implant is arranged at the at least one stitching member 32 by e.g. twisting the implant into place. Other ways of arranging the implant at the least one stitching member 32 is by e.g. inserting, pushing, pulling or similar known methods.

In yet another example the method further comprising collapsing the stitching device to said collapsed mode allowing for retraction of the stitching device from the patient. By collapsing the stitching device 1 the operator can retract the device 1 from the patient after the securing of the thread 51 and/or implant 50.

The present invention has been described above with reference to specific embodiments. However, other embodiments than the above described are equally possible within the scope of the invention. The different features and steps of the invention may be combined in other combinations than those described. The scope of the invention is only limited by the appended patent claims.

More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used.

The invention claimed is:

1. A single action annuloplasty stitching device for stitching at a stitch site in a patient, comprising,
    a support structure comprising an elongate center support extending along an axial direction between a proximal end and a distal end,
        a stitching arrangement comprising,
        at least one elongate linkage section being rotationally attached at a support end of the at least one elongate linkage section to the elongate center support, and
        at least one stitching member elongate pivotably arranged at a stitch end of the at least one elongate linkage section and being movable along while being parallel to said axial direction by a pivoting action of the at least one elongate linkage section, and
        wherein said at least one stitching member is arranged adjacent and parallel to said elongate center support in a collapsed mode of said stitching arrangement;
    wherein the at least one stitching member comprises a needle and a thread guide for a thread, said thread guide being movably connected to said needle or said at least one elongate linkage section for being movable to an open state having an opening between said needle and said thread guide for forming a thread loop path around said opening;
    wherein the thread guide comprises at least two guide levers rotationally joined at a respective joining end, whereby said at least two guide levers are movable to an open state having a first and a second opening for providing a first and a second thread loop path around said first and second openings.

2. The single action stitching device according to claim 1, wherein the stitching arrangement is movably arranged from said collapsed mode, wherein the at least one elongate linkage section is parallel arranged adjacent to the elongate center support, to a deployed mode, wherein the at least one elongate linkage section is arranged substantially perpendicular to the elongate center support and the at least one stitching member is arranged substantially parallel to the elongate center support.

3. The single action stitching device according to claim 1, wherein the support structure further comprises;
    an upper connection member arranged adjacent the distal end of the elongate center support,
    a lower connection member arranged on the elongate center support proximal of the upper connection member, said upper and/or lower connection members being connected to said at least one elongate linkage section, and wherein the upper and/or lower connection members are movable relative to each other.

4. The single action stitching device according to claim 3, wherein each of said at least one elongate linkage section comprises,
    an upper bar rotationally connected to the upper connection member at a support end of the upper bar,
    a lower bar rotationally connected to the lower connection member at a support end of the lower bar, and wherein the upper and lower bars are connected to the at least one stitching member at their stitch ends.

5. The single action stitching device according to claim 4, wherein the upper bar comprises a recess along at least a part of its length and wherein the recess is large enough to partly surround the lower bar in the collapsed mode.

6. The single action stitching device according to claim 4, wherein the needle of the at least one stitching member has a blunt end and a sharp end, and wherein the blunt end is rotationally connected to the upper bar and wherein the lower bar is slidably connected to the needle closer to the sharp end than the upper bar, allowing for the needle to be arranged parallel to the elongate center support in the collapsed mode and in a deployed mode.

7. The single action stitching device according to claim 1, wherein said opening between said needle and said thread guide is adapted to receive and guide an annuloplasty implant.

8. The single action stitching device according to claim 1, wherein each of said respective joining ends are pivotably connected to said needle at a pivoting joint, whereby said at least two guide levers are movable to a closed state in which the at least two guide levers are parallel to said needle.

9. The single action stitching device according to claim 8, wherein the at least two guide levers are releasable connected to the needle at said pivoting joint.

10. The single action stitching device according to claim 1, wherein said thread guide is rotationally linked to said at least one elongate linkage section, whereby said thread guide is movable to said open state by moving said at least one elongate linkage section.

11. The single action stitching device according to claim 1, wherein said needle and/or said thread guide comprises a cut-out for receiving said thread, said cut-out releasably securing said thread.

12. The single action stitching device according to claim 1, comprising a plurality of said stitching arrangements connected to said support structure such that said stitching members are arranged along a three-dimensional path along which an implant partially extends.

13. The single action stitching device according to claim 1, wherein the length of the at least one elongate linkage section substantially correspond to the radius of an annuloplasty ring.

\* \* \* \* \*